(12) United States Patent
Littman

(10) Patent No.: US 12,067,534 B2
(45) Date of Patent: Aug. 20, 2024

(54) MAINTENANCE MANAGEMENT SYSTEM FOR LABORATORY INSTRUMENTATION

(71) Applicant: Beckman Coulter, Inc., Brea, CA (US)

(72) Inventor: Brian J. Littman, Prior Lake, MN (US)

(73) Assignee: Beckman Coulter, Inc., Brea, CA (US)

( * ) Notice: Subject to any disclaimer, the term of this patent is extended or adjusted under 35 U.S.C. 154(b) by 378 days.

(21) Appl. No.: 17/381,660

(22) Filed: Jul. 21, 2021

(65) Prior Publication Data
US 2021/0350338 A1 Nov. 11, 2021

Related U.S. Application Data

(63) Continuation of application No. PCT/US2020/014702, filed on Jan. 23, 2020.

(60) Provisional application No. 62/796,815, filed on Jan. 25, 2019.

(51) Int. Cl.
G06Q 10/20 (2023.01)
G06Q 10/0631 (2023.01)

(52) U.S. Cl.
CPC ....... *G06Q 10/20* (2013.01); *G06Q 10/06315* (2013.01)

(58) Field of Classification Search
CPC .. G06Q 10/20; G06Q 10/06315; G06Q 10/00; G16H 10/40; G16H 40/40
See application file for complete search history.

(56) References Cited

U.S. PATENT DOCUMENTS

| 9,342,807 | B2 | 5/2016 | Yamaguchi et al. |
| 11,195,611 | B2 | 12/2021 | Davis |
| 11,199,557 | B2 | 12/2021 | Parker et al. |
| 2005/0143956 | A1 | 6/2005 | Long et al. |

(Continued)

FOREIGN PATENT DOCUMENTS

WO 2020223616 A2 11/2020

OTHER PUBLICATIONS

ELab—Remote Electronics Lab in Real Time Manuel E. Macías, Israel Méndez Electrical and Computing Engineering, ITESM Campus Monterrey Av. Garza Sada 2501, 64849 Monterrey, N.L. México (Year: 2007).*

(Continued)

*Primary Examiner* — Alexandru Cirnu
(74) *Attorney, Agent, or Firm* — Frost Brown Todd LLP

(57) ABSTRACT

A geospatial maintenance server collects information from lab instruments such as usage information, instrument uptime, operational performance, and other characteristics. Such information may be used to identify upcoming maintenance needs for lab instruments, including usage based preventative maintenance, and unanticipated degradation based maintenance. A geospatial maintenance interface is provided that allows a user to select a certain country, region, state, or other geographic area to view information on lab instruments and maintenance needs within that area. The interface may display graphs showing uptime for various time periods, comparisons to uptime in other areas, maps with symbols indicating areas and types of maintenance needs, and per-device descriptions of maintenance needs. The interface may also be used to automate efficient and economical assignment of technicians to address maintenance tasks.

18 Claims, 5 Drawing Sheets

(56) References Cited

U.S. PATENT DOCUMENTS

| | | |
|---|---|---|
| 2012/0290104 A1 | 11/2012 | Holt et al. |
| 2013/0212512 A1* | 8/2013 | Frenz ................ H04L 67/06 715/771 |
| 2016/0078695 A1* | 3/2016 | McClintic ........... G07C 5/0816 701/29.4 |
| 2017/0203030 A1* | 7/2017 | Brewer ............ A61M 5/14244 |
| 2019/0036178 A1* | 1/2019 | Karner ............. H02J 13/00002 |
| 2019/0271713 A1 | 9/2019 | Heinemann et al. |
| 2019/0376991 A1 | 12/2019 | Rudorfer et al. |
| 2020/0013501 A1* | 1/2020 | Page ..................... G08B 21/24 |
| 2020/0382599 A1 | 12/2020 | Knafel et al. |
| 2020/0411176 A1 | 12/2020 | Hadorn et al. |
| 2021/0020307 A1* | 1/2021 | Bhimavarapu .... G06Q 10/1097 |
| 2021/0081839 A1 | 3/2021 | Heydlauf |
| 2022/0208364 A1 | 6/2022 | Naik et al. |

OTHER PUBLICATIONS

International Search Report and Written Opinion dated May 13, 2020 for International Application No. PCT/US2020/014702, 9 pages.

\* cited by examiner

MAINTENANCE MANAGEMENT SYSTEM FOR LABORATORY INSTRUMENTATION

PRIORITY

This application is a continuation of International Application Number PCT/US20/14702, filed in the United States Patent Office on Jan. 23, 2020, titled "Maintenance Management System for Laboratory Instrumentation," which is also related to and claims the benefit of previously filed provisional application 62/796,815, filed Jan. 25, 2019, and titled "Maintenance Management System for Laboratory Instrumentation." Those applications are hereby incorporated by reference in their entirety.

FIELD

The disclosed technology pertains to systems, methods, and interfaces for providing maintenance features for diagnostic instrumentation, and in particular geospatial maintenance feature for diagnostic instruments.

BACKGROUND

Diagnostic instrumentation in general may have various maintenance needs while in service in order for continuous and accurate functioning and providing accurate results. Typically, some maintenance needs may be predictable, such as, where certain components need be cleaned or replaced based upon a known maintenance schedule that may be measured in number of days in service or number of performed testing cycles or operations. Usually, some other maintenance needs may be less predictable, and may arise due to an unforeseen failure or degradation of a component. Usually, providing instrument maintenance to hundreds or thousands of instruments spread across a large geographic area such as a country or a region of a country or across multiple continents may be challenging to distribute a limited number of maintenance technicians in a way that all predictable maintenance issues may be addressed in a timely manner. And, this task may be further complicated by a more sudden and immediate need for unpredictable maintenance arising across an area.

SUMMARY

Embodiments of the present disclosure provide for determining and addressing lab instrument maintenance needs across a geospatial area or across multiple geographical areas.

One embodiment may be to provide geospatial maintenance system comprising a maintenance server, the maintenance server configured to receive from a plurality of instruments located in a specific region or multiple regions a set of instrument use data and a set of instrument performance data. In a further embodiment, the maintenance server may be configured to determine, for each of the plurality of instruments, any upcoming maintenance requirements based on the set of instrument use data and the set of instrument performance data. In a further embodiment, the maintenance server may be configured to, based on the upcoming maintenance requirements, provide to a user over an interface the plurality of instruments and a mapping of the upcoming maintenance requirements in the specific region or multiple regions for maintenance to be performed on the plurality of instruments. Other embodiments are also disclosed.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
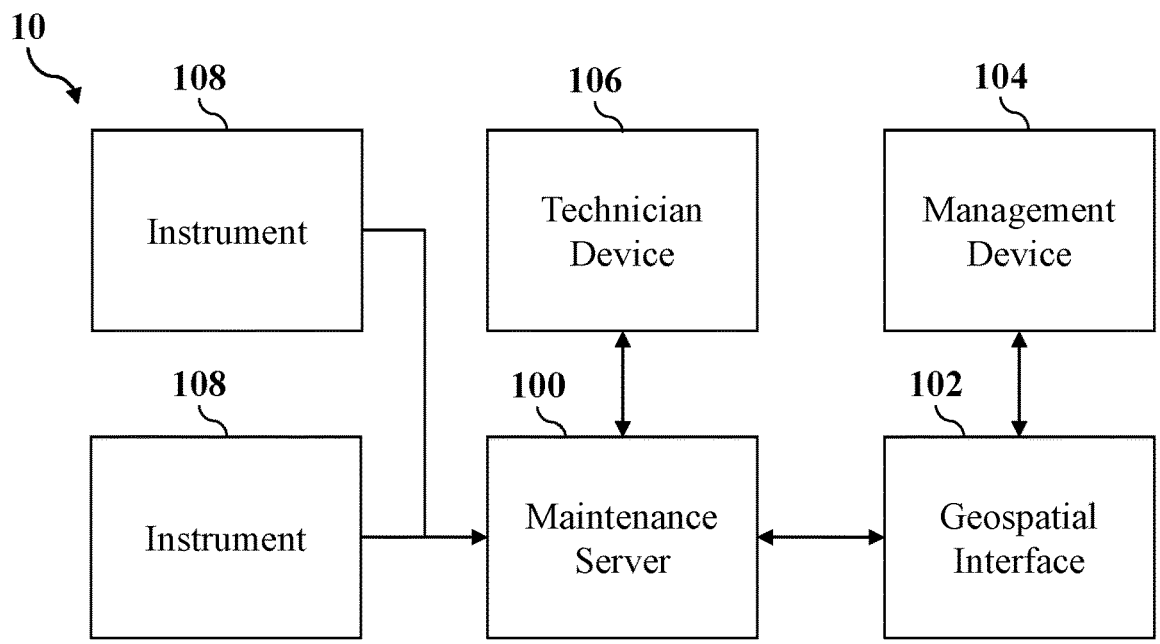
FIG. 1 is an exemplary architecture which may be used in some embodiments.

Some lab instrument maintenance may be needed based on time or usage based intervals. Efficiently providing maintenance for a large number of instruments spread across a geographic area can be difficult even where those needs are predictable. This task can be further complicated when maintenance requirements arise unpredictably. With a mixture of predictable and unpredictable maintenance requirements, there may be times where a technician provides regular preventative maintenance to an instrument, and then must return within days or weeks to service the same instrument due to unanticipated reduced performance. To address this, it may be advantageous to proactively identify instruments that are likely to have a performance based maintenance requirement arise. However, with conventional approaches it may not be feasible to make such determinations.

According to a first aspect, some embodiments may provide a method comprising receiving from a plurality of instruments located in a specific region or multiple regions a set of instrument use data and a set of instrument performance data. In some embodiments, such a method may further comprise determining, for each of the plurality of instruments, whether there are any upcoming maintenance requirements based on the set of instrument use data and the set of instrument performance data. In some embodiments, such a method may further comprise, based on the upcoming maintenance requirements, providing to a user over an interface the plurality of instruments and a mapping of the upcoming maintenance requirements in the specific region or multiple regions for maintenance to be performed on the plurality of instruments.

According to a second aspect, some embodiments may provide a method such as described in the context of the first aspect wherein the set of instrument use data comprises, for each instrument of the plurality of instruments, a usage indicator describing a number of test cycles performed by that instrument during a period of time. In some such methods, the set of instrument performance data may comprise, for each instrument of the plurality of instruments, a performance indicator that describes the operational performance of a component of that instrument. In some such methods, the performance indicator may be selected from the group consisting of: flow rate of a pump, temperature of an electrical component, and power consumption of an electrical component.

According to a third aspect, some embodiments may provide a method such as described in the context of any of the first or second aspects which may further comprise displaying a map of the specific region or multiple regions. In some such embodiments, the method may further comprise displaying a first set of symbols on the map, wherein each symbol of the first set of symbols indicates a location and a number of actual maintenance requirements, wherein the actual maintenance requirements are selected from the upcoming maintenance requirements. In some such embodiments, the method may further comprise displaying a second set of symbols on the map, wherein each symbol of the second set of symbols indicates a location and a number of potential maintenance requirements. In some such embodiments, the potential maintenance requirements may be selected from the upcoming maintenance requirements. In some such embodiments, each symbol of the first set of symbols may comprise a size that may be determined based upon the number of actual maintenance requirements at the location.

According to a fourth aspect, some embodiments may provide a method such as described in the context of any of the first through third aspects which may further comprise displaying a first graph line showing an uptime for the plurality of instruments over a period of time. In some such embodiments, the method may further comprise displaying a second graph line showing, over the period of time, an uptime for a set of high uptime instruments. In some such embodiments, the method may further comprise displaying a third graph line showing, over the period of time, an uptime for a set of low uptime instruments.

According to a fifth aspect, some embodiments may provide a method such as described in the context of any of the first through fourth aspects which further comprises displaying a device maintenance view for each instrument of the plurality of instruments. In some such embodiments, the method may further comprise displaying a set of maintenance requirements and a set of maintenance statuses for each instrument of the plurality of instruments. In some such embodiments, each of the set of maintenance statuses may be associated with a maintenance requirement of the set of maintenance requirements. In some such embodiments, each of the set of maintenance statuses comprises an indicator positioned on that maintenance status that indicates an immediacy of that maintenance requirement.

According to a sixth aspect, some embodiment may provide a method such as described in the context of any of the first through fifth aspects, wherein the upcoming maintenance requirements may comprise a set of actual maintenance requirements and a set of potential maintenance requirements. In some such embodiments, the method may further comprise identifying the set of actual maintenance requirements based on the set of instrument use data. In some such embodiments, the method may further comprise identifying the set of potential maintenance requirements based on the set of instrument performance data.

According to a seventh aspect, some embodiments may provide a method such as described in the context of any of the first through sixth aspects wherein the upcoming maintenance requirements may comprise a set of potential maintenance requirements. In some such embodiments, the method may comprise maintaining a set of historical performance data for each instrument of the plurality of instruments. In some such embodiments, the method may comprise after new performance data may be received for an instrument of the plurality of instruments, comparing the new performance data to the set of historical performance data for that instrument to determine a performance change. In some such embodiments, the method may comprise where the performance change indicates a significant change, adding a potential maintenance requirement to the set of potential maintenance requirements, wherein the potential maintenance requirement may be associated with that instrument and describes a component of that instrument associated with the performance change.

According to an eighth aspect, some embodiments may provide a method such as described in the context of the seventh aspect which may comprise determining a first standard deviation of the set of historical performance data for that instrument over a first period of time. In some such embodiments, the method may also comprise determining a second standard deviation of the new performance data for that instrument over a second period of time. In some such embodiments, the method may also comprise determining that the performance change indicates a significant change when the difference between the first standard deviation and the second standard deviation exceeds a configured threshold.

According to a ninth aspect, some embodiments such as described in the context of the eight aspect may provide a method in which the first period of time may be a preceding 24 hour period. In some such embodiments, the second period of time may be a 72 hour period preceding the 24 hour period.

According to a tenth aspect, some embodiments such as described in the context of any of the seventh through ninth aspects may provide a method in which the set of historical performance data may comprise performance data associated with one or more components of that instrument. In some such embodiments, the method may comprise determining the performance change for each component of the one or more components. In some such embodiments, the method may comprise, when adding the potential maintenance requirement for the component, determining a priority for the potential maintenance requirement based on the magnitude of the performance change and a type of the component.

According to an eleventh aspect, some embodiments may provide a method such as described in the context of any of the first through tenth aspects in which each instrument from the plurality of instruments is a diagnostic instrument.

According to a twelfth aspect, some embodiments may provide a geospatial maintenance system configured to perform a method as described in the context of any of the first through eleventh aspects.

According to a thirteenth aspect, some embodiments may provide a system comprising a maintenance server configured to perform the steps of the methods described in the context of any of the first through eleventh aspects.

Corresponding computer readable media storing instructions for performing steps of methods such as described in the context of any of the first through eleventh aspects could also be implemented without undue experimentation by those of ordinary skill in the art based on this disclosure. Accordingly, the preceding description of potential embodiments and aspects should be understood as being illustrative only, and should not be treated as limiting.

FIG. 1 shows an exemplary architecture which may be used in one embodiment. A maintenance system 10 includes a maintenance server 100, a geospatial interface 102, a management device 104, a technician device 106, and at least one instrument 108. In one embodiment, maintenance server 100 may be configured to receive information from instruments 108 describing their use and other characteristics. In one embodiment, maintenance server 100 may be configured to provide geospatial interface 102 to users via management device 104. In one embodiment, maintenance server 100 may be configured to communicate with technician device 106 based upon interactions of the management device 104 with the geospatial interface 102.

In an example embodiment, management device 104 and technician device 106 may be smartphones, tablets, or computers. In an example embodiment, geospatial interface 102 may be provided to management device 104 as a web site, mobile application, or other software application. In an example embodiment, instrument 108 may be a diagnostic testing instrument within a laboratory or other setting. In an example embodiment, maintenance system 10 may include hundreds or thousands of instrument 108 spread across a geographic area such as a city, stage, or region of a country.

Figure 2:
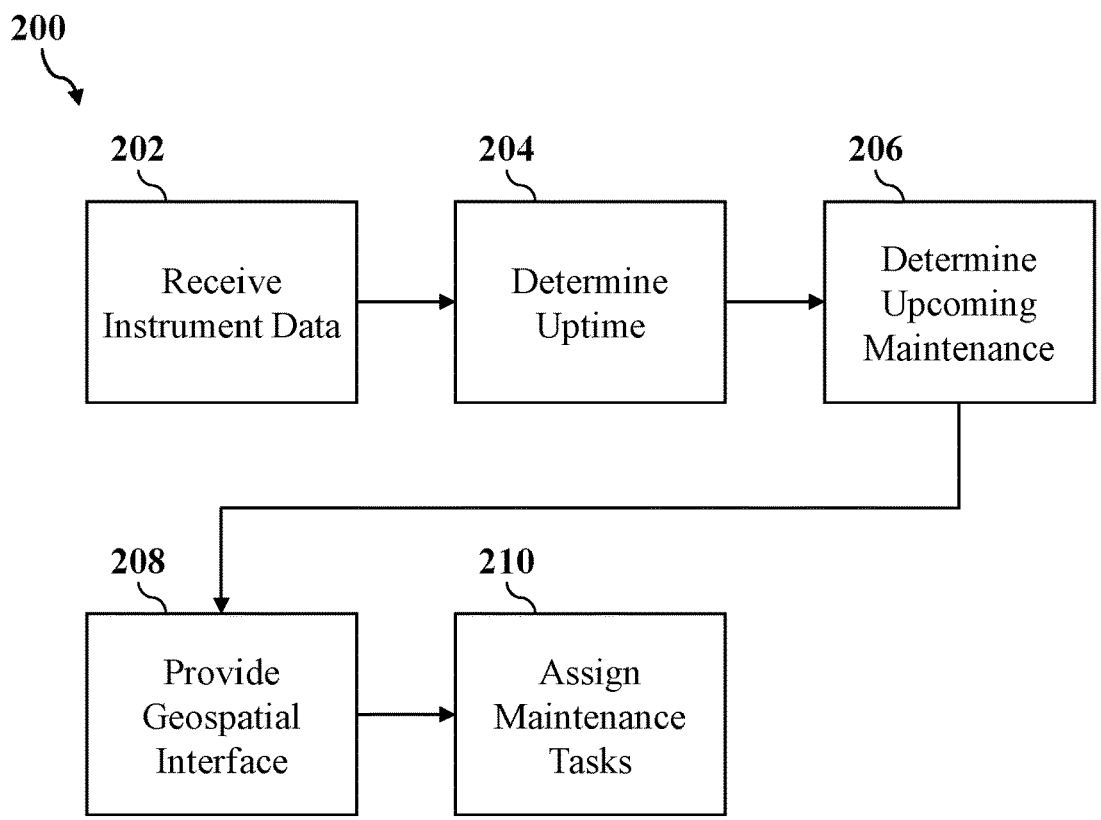
FIG. 2 is a flowchart showing high level steps of an exemplary process which may be used in some embodiments to provide geospatial maintenance management.

FIG. 2 is a flowchart showing high level steps of an exemplary process 200 which may be used in some embodiments to provide geospatial maintenance management. In an example embodiment, process 200 may be performed by or with maintenance system 10. In step 202, instrument data is received. In step 204, instrument uptime is determined. In step 206, upcoming maintenance needs are determined. For the sake of clarity, it should be understood that an upcoming maintenance requirement may be described herein as a "need' or a "requirement, and that these terms may be used interchangeably without indicating that a maintenance task being described is strictly required for continued operation of a particular instrument, or whether the described task is merely desirable or beneficial for continued operation of the instrument. In step 208, a geospatial interface is provided. In step 210, maintenance tasks may be assigned.

In one embodiment, receiving instrument data at step 202 may include maintenance server 100 receiving information from, or accessing information on one or more instruments 108 and storing it in a database, file system, or other data repository accessible to maintenance server 100. In an example embodiment, received data may include a unique identifier or description of the instrument from which data is received, a description of the location where the instrument is in use, an indication that the instrument was in use during a time interval, an indication the instrument was unavailable for use due to an error or maintenance issue, an indication that the instrument completed a test cycle or another indication of usage, instrument performance and specification data for one or more components, and other similar information. In an example embodiment, data may be received as it is generated by use of instrument 108. In another example embodiment, data may be received from time-to-time based on a schedule.

In one embodiment, determining uptime at step 204 may include analyzing received data to determine uptime for one or more instruments over various periods of time and associating that data with other instrument data in a data repository. In one embodiment, determining upcoming maintenance needs at step 206 may include analyzing received data to identify actual upcoming maintenance needs based upon usage or time intervals. In one embodiment, determining upcoming maintenance needs at step 206 may include analyzing received data to identify potential upcoming maintenance needs based upon performance data of one or more components of the instrument. In one embodiment, providing the geospatial interface at step 208 may include providing software and data to render maintenance information and interactive features on a device such as management device 104. In one embodiment, assigning maintenance tasks at step 210 may include using received information along with information on technician availability and location to automatically or semi-automatically assign maintenance tasks to technicians.

Figure 3A:
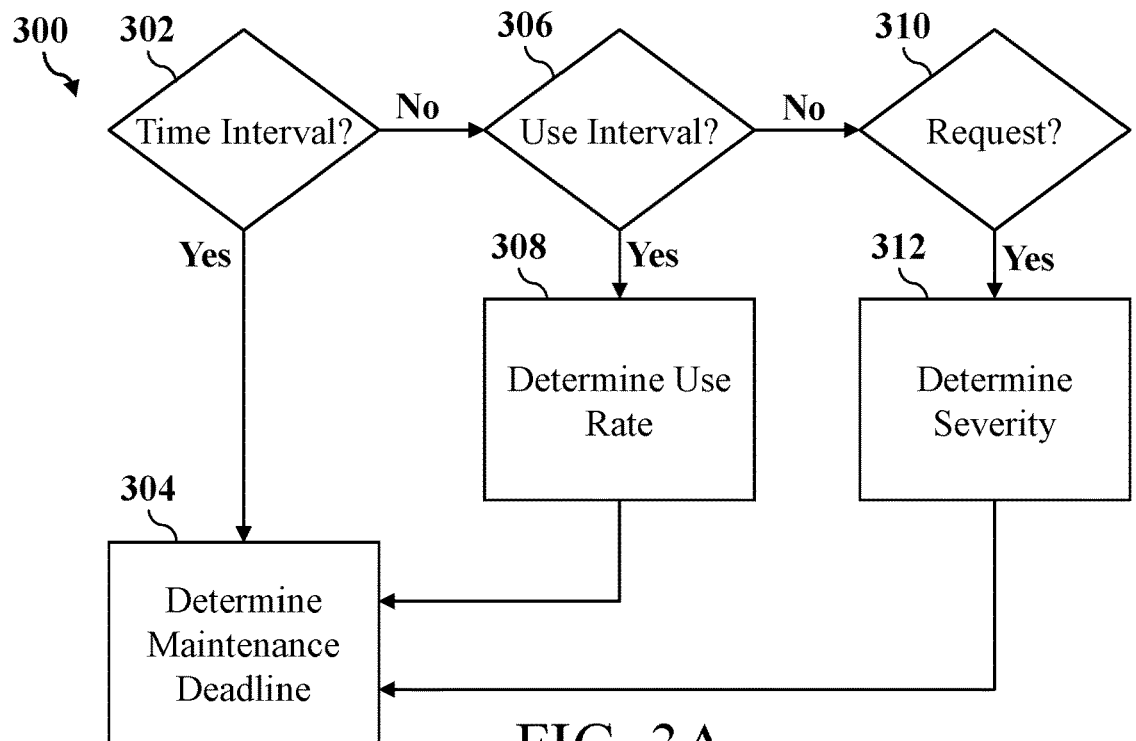
FIG. 3A is a flowchart showing an exemplary process which may be used in some embodiments to identify actual upcoming maintenance needs.

FIG. 3A is a flowchart showing an exemplary process 300 which may be used in some embodiments to identify actual upcoming maintenance needs. In an example embodiment, process 300 may be performed by or with maintenance system 10. In a step 302, whether there is any time interval based maintenance requirement is determined. In a step 304 a deadline for a maintenance task is determined. In a step 306 whether there is a usage based maintenance requirement is determined. In a step 308 a usage rate is determined. In a step 310 whether there are any direct maintenance requests is determined. In a step 312 a severity of a request is determined.

In one embodiment, process 300 may be performed each time new information related to instrument maintenance is received by maintenance server 100. In one embodiment, process 300 may be performed from time-to-time based on a schedule. In one embodiment, determining whether there are any time interval based maintenance needs at step 302 may include analyzing uptime and service information from instrument 108 to determine a period of time that it has been in service, checking a maintenance record to determine the types and dates of prior maintenance, and checking a time based maintenance interval configuration. In one embodiment, such information may be used to determine that upcoming maintenance needs exist, and to determine a completion deadline for those needs at step 304.

In one embodiment, determining whether there are any usage based maintenance intervals upcoming at step 306 may include analyzing service and usage information from instrument 108 to determine an amount of usage of instrument 108 during a period of time. In one embodiment, determining a use rate of instrument 108 at step 308 may include analyzing usage information from instrument 108 over a period of weeks or months to determine an average rate at which it is used during a particular period of time. In one embodiment, determining a maintenance deadline for an upcoming usage based maintenance at step 304 could include determining an amount of usage since a particular maintenance task was performed, an amount usage until that maintenance task should be performed again, and an approximate date that maintenance task should be completed by based on the average use rate.

In one embodiment, determining whether there are any maintenance requests at step 310 may include checking records in a data repository to determine if any maintenance requests or tickets have been directly submitted for instruments. In one embodiment, determining a severity of a maintenance request at step 312 may include determining a date the request was created and a type or magnitude of the maintenance issue described in the request. In one embodiment, determining a deadline for the request at step 304 may include using the request date and the issue type to determine a deadline for when the request should be addressed. In an example embodiment, whenever a deadline is determined for a maintenance it may be saved and associated with the instrument in a data repository so that it may be used to provide geospatial interface 102. In one embodiment, geospatial interface 102 may be used to view maintenance needs and deadlines whether they are submitted or requested by users, based upon a time interval, based upon a usage interval, or based upon another interval or circumstance.

Figure 3B:
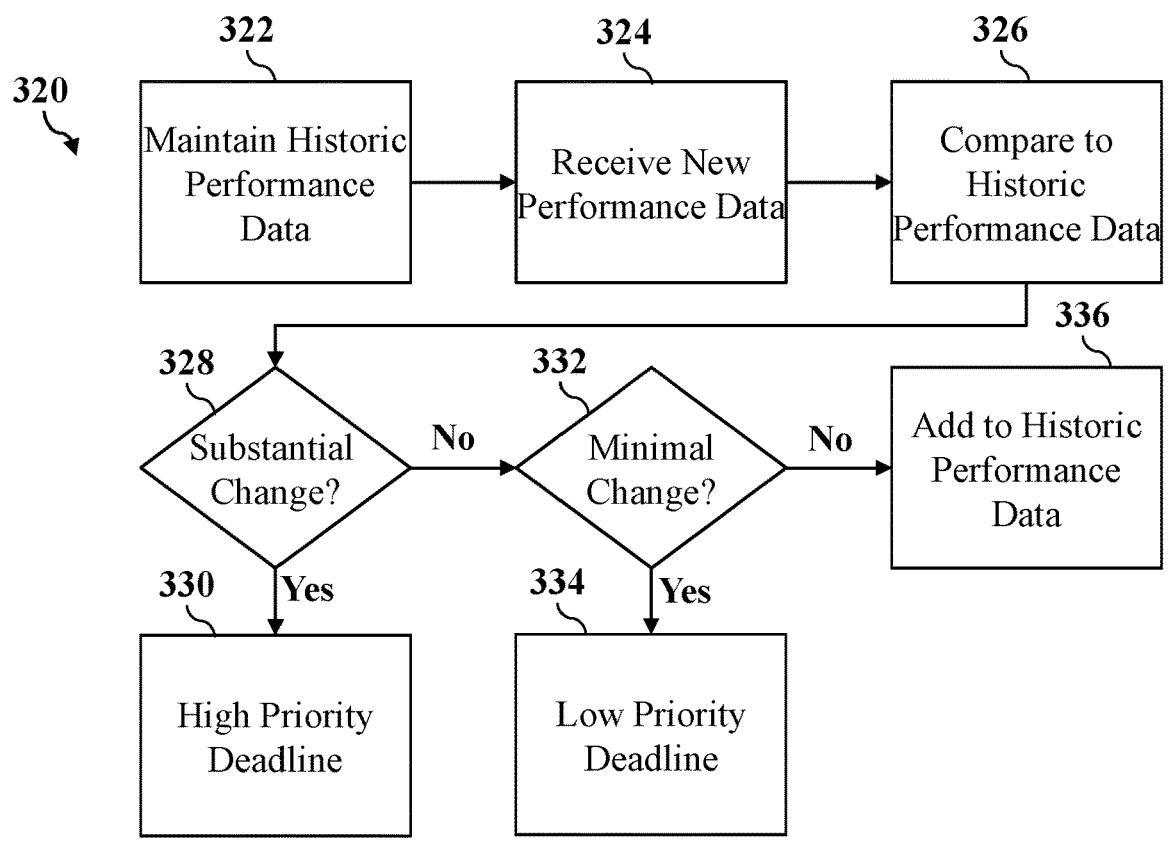
FIG. 3B is a flowchart showing an exemplary process which may be used in some embodiments to identify potential upcoming maintenance needs.

FIG. 3B is a flowchart showing an exemplary process 320 which may be used in some embodiments to identify potential upcoming maintenance needs. In an example embodiment, process 320 may be performed by or with maintenance system 10. In a step 322, historic performance data is maintained. In a step 324, new performance data is received. In a step 326, historic performance data is compared to new performance data. In a step 328, it is determined there is a substantial change in performance. In a step 330, a maintenance task with a high priority is created. In a step 332, it is determined whether there is a minimal change in performance. In a step 334, a maintenance task with a low priority is created. In a step 336, the new performance data is added to the historic performance data.

In one embodiment, maintaining historic performance data at step 322 may include saving performance data for one or more components of instrument 108 as it is received by maintenance server 100. In an example embodiment, received data may include data from a sensor, instrument controller, instrument power supply, or other component of instrument 108 describing operational characteristics of instrument 108. In an example embodiment, received data may include data describing flow rate, vacuum pressure, or power consumption of a pump component. In an example embodiment, received data may include data describing linear or rotational movement speed or power consumption of an electric motor component. In an example embodiment, received data may include a measured operational temperature or electrical power consumption of a pump, motor, processor, storage drive, illuminating device, or other component of instrument 108 that may be susceptible to damage or degradation as a result of undesirable temperature conditions.

In an example embodiment, received data may include other similar information describing measurable operational characteristics of instrument 108. In an example embodiment, received data may be produced by an integral component of instrument 108 such as a processor, controller, or power supply, or a temperature sensor or flow rate sensor integrated with a component or fluid supply line. In an example embodiment, received data may be produced by an external or additional component of instrument 108 such as an inline flow sensor, an installed temperature sensor, or an inline current sensor added to instrument 108.

In one embodiment, receiving new performance data at step 324 may include receiving new data similar to that being maintained as historic performance data based upon recent uses of instrument 108. In one embodiment, new data may be received as it is produced by instrument 108. In one embodiment, new data may be received from time-to-time based upon a schedule for updating data from instrument 108. In one embodiment, received new performance data may be converted into similar formats or software objects as stored historic performance data.

In one embodiment, comparing newly received performance data to historic performance data in step 326 may include, for a configured period of time, determining an average performance for a certain characteristic or component of instrument 108 and comparing the newly receive performance data for the same characteristic or component to the past performance data. In an example embodiment, a comparison may be made by determining and comparing standard deviations of newly received performance data and past performance data. In an example embodiment, a period of time for which the average performance is determined as part of a comparison may be 72 hours. In an example embodiment, a period of time for which the average performance is determined may exclude any time period where it is determined that the instrument 108 performed abnormally. In an example embodiment, a period of time used in the comparison may be a period of time immediately prior to a period of time of the newly received data. In an example embodiment, a period of time used in the comparison may be a period of time from when instrument 108 was newly installed or newly configured. In an example embodiment, new performance data may describe flow rate produced by a vacuum pump of instrument 108 over the past 24 hours, and comparison historic performance data may describe flow rate produced by the same vacuum pump of instrument 108 over a 72 hour period preceding the past 24 hours.

In one embodiment, determining whether there is substantial change at step 328 may include using data from the prior comparison to determine whether a threshold indicating a substantial change is exceeded for a comparison of the performance data. In an example embodiment, this may include comparing a previously determined standard deviation to a standard deviation threshold for indicating whether a significant change in performance occurred, and whether it was substantial. In an example embodiment, this may include comparing a new performance characteristic to an average performance characteristic to determine if the difference exceeds a change threshold indicating a significant and substantial change occurred. In an example embodiment, a change qualifying as a substantial change may be a percentage difference in actual value or standard deviation. In an example embodiment, the particular threshold for a substantial change may depend upon the particular component associated with the comparison. In an example embodiment, a high precision pump may have a low threshold for what is a substantial change, while a high volume general purpose pump may have a relatively higher threshold for what is a substantial change.

In one embodiment, creating a maintenance task with a high priority or deadline for completion at step 330 may include creating a maintenance record indicating the instrument for which the substantial change in performance was detected, describing the change in performance, and associating the maintenance record with a deadline for completion. In an example embodiment, a maintenance record may be created on maintenance server 100. In an example embodiment, maintenance server 100 may also be configured to provide a maintenance or service ticketing software separate from geospatial interface 102, and creating a high priority maintenance record may include creating a service ticket for that software. In an example embodiment, a high priority deadline may be a deadline that will be completed within between about one day and about fifteen days. In one example embodiment, a deadline for completion of a high priority maintenance task may be selected based upon a predicted cost of damages to instrument 108 over a time period based on the substantial change in performance of instrument 108, wherein the high priority deadline is selected to provide intervening maintenance and avoid the cost of damages.

In one embodiment, determining whether there is a minimal but significant change in performance at step 332 may include using data from the prior comparison to determine whether a threshold indicating a minimal change has been exceeded in the comparison of the performance data. In an example embodiment, this may include comparing a previously determined standard deviation to a standard deviation threshold for indicating whether a significant change in performance occurred, and whether it was minimal but not substantial. In an example embodiment, this may include comparing a new performance characteristic to an average performance characteristic to determine if the difference exceeds a change threshold indicating a significant but minimal change occurred. In an example embodiment, a change qualifying as a minimal change may be a percentage difference in actual value or standard deviation. In an example embodiment, the particular threshold for a minimal change may depend upon the particular component associated with the comparison. In an example embodiment, a high precision pump may have a very low threshold for what is a minimal change, while a high volume general purpose pump may have a relatively higher threshold for what is a minimal change.

In one embodiment, creating a maintenance task with a low priority or deadline for completion at step 334 may include creating a maintenance record indicating the instrument for which the minimal change in performance was detected, describing the change in performance, and associating the maintenance record with a deadline for completion. In an example embodiment, a maintenance record may be created on maintenance server 100. In an example embodiment, maintenance server 100 may also be configured to provide a maintenance or service ticketing software separate from geospatial interface 102, and creating a low priority maintenance record may include creating a service ticket for that software. In an example embodiment, a low priority deadline may be a deadline that will be completed within between about ten days and about forty days. In one example embodiment, a deadline for completion of a low priority maintenance task may be selected based upon a predicted cost of damages to instrument 108 over a time period based on the substantial change in performance of instrument 108, wherein the low priority deadline is selected to provide intervening maintenance and avoid the cost of damages.

In one embodiment, adding newly received performance data to historic performance data at step 336 may include, where received performance data does not indicate a substantial or minimal change or degradation in performance, updating a maintained set of historic performance data to include the newly received performance data. In an example embodiment, where a historic performance comparison is provided based upon average performance over a preceding 72 hour period, this may include recalculating the 72 hour performance of instrument 108 to discard an older set of performance data, and include the more recent performance data.

Figure 4:
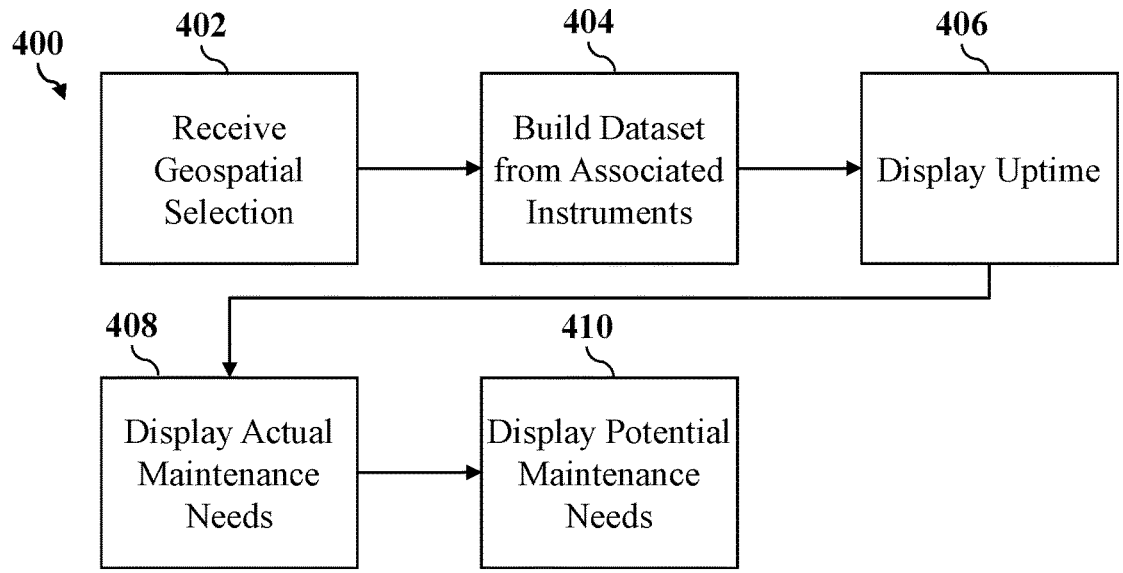
FIG. 4 is a flowchart showing an exemplary process which may be used in some embodiments to provide a geospatial maintenance interface.

FIG. 4 is a flowchart showing an exemplary process 400 which may be used in some embodiments to provide a geospatial maintenance interface. In an example embodiment, process 400 may be performed by or with maintenance system 10. In a step 402, a geospatial region selection is received. In a step 404, a dataset is built for the associated instruments. In a step 406, a set of uptime data is displayed. In a step 408, a set of actual maintenance information is displayed. In a step 410, a set of potential maintenance information is displayed.

In one embodiment, receiving a geospatial selection at step 402 may include receiving a selection from a user indicating a geographic area. In an example embodiment, the selection may include one or more of a selection by country, region, state, city, zip-code, or another geographic indicator. In an example embodiment, a selection may be further confined based upon a selection of a warranty status, for where a user may wish to only view maintenance tasks related to instruments that are still covered by a manufacturer or other warranty. In an example embodiment, the selection may be received via one or more of a web site, a mobile application, a web service, or a desktop software application. In an example embodiment, the selection may be received automatically based upon one or more of a user account or identity for a user accessing geospatial interface 102 and a detected user location for a user accessing geospatial interface 102.

In one embodiment, building a dataset from associated instruments at step 404 may include identifying every instrument such as instrument 108 that meets the criteria of the received selection. In one embodiment, the built dataset may include a description of any maintenance task associated with any matching instrument, a description of every matching instrument, and operational characteristics and performance data of every matching instrument. In an example embodiment, the built dataset may include data relating to instrument use and uptime for every matching instrument.

In one embodiment, displaying uptime of the matching instruments at step 406 may include aggregating or otherwise combining use and uptime data for every matching instrument and displaying such data to a user via an interface and display. In an example embodiment, uptime data for matching instruments may be displayed as a comparison to uptime data for another set or population of instruments. In an example embodiment, uptime data for matching instruments may be displayed as a comparison to uptime data for all instruments viewable by maintenance system 10. In an example embodiment, uptime data may be displayed as a graph or other visual data structure. In an example embodiment, uptime data may be displayed for one or more time periods, individually or simultaneously, based upon a user selection or other configuration. In an example embodiment, time periods for uptime data may include 24 hours, 10 days, 30 days, and 90 days. In an example embodiment, uptime may be displayed as a percentage of matching instruments, during a time period, that were available for use. In an example embodiment, uptime may be displayed as a percentile representing the relative reliability of the matching instruments within a global population of instruments for uptime. In an example embodiment, uptime data may be displayed using uptime interface 500 of FIG. 5A.

In one embodiment, displaying actual maintenance needs at step 408 may include displaying information describing actual maintenance needs identified by maintenance system 10. In an example embodiment, actual maintenance needs include one or more of time interval based maintenance needs and their deadlines, use based maintenance needs and their deadlines, and directly requested maintenance needs and their deadlines. In an example embodiment, actual maintenance needs include maintenance needs identified according to one or more of the steps of FIG. 3A. In an example embodiment, actual maintenance needs may be displayed with a description of the maintenance need, an individual instrument associated with the maintenance need, and an indicator of the deadline for the maintenance need. In an example embodiment, actual maintenance needs may be displayed using one or more of maintenance map interface 520 of FIG. 5B or detailed maintenance interface 540 of FIG. 5C.

In one embodiment, displaying potential maintenance needs may include displaying information describing potential maintenance needs that are predicted and identified by maintenance system 10. In an example embodiment, potential maintenance needs include one or more of high priority maintenance needs and low priority maintenance needs and their respective deadlines. In an example embodiment, potential maintenance needs may be identified based upon a performance degradation comparison. In an example embodiment, potential maintenance needs include maintenance needs identified according to one or more of the steps of FIG. 3B. In an example embodiment, potential maintenance needs may be displayed with a description of the need, an individual instrument associated with the need, and an indicator of the deadline for the need. In an example embodiment, potential maintenance needs may be displayed using one or more of maintenance map interface 520 and detailed maintenance interface 540.

Figure 5A:
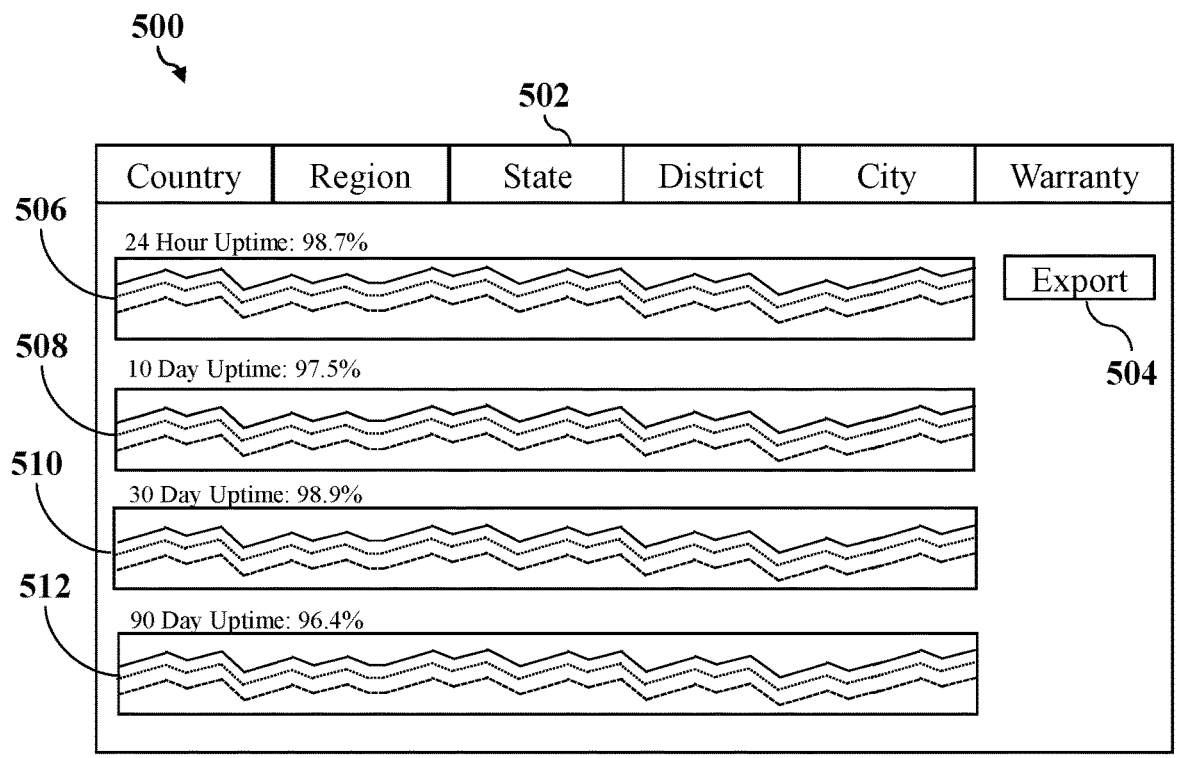
FIG. 5A is a diagram showing an exemplary uptime interface that may be provided as part of the geospatial maintenance interface of FIG. 4.

FIG. 5A is a diagram showing an exemplary uptime interface 500 that may be provided as part of the geospatial maintenance interface of FIG. 4. The uptime interface 500 includes a region selection 502, an export button 504, a first uptime graph 506, a second uptime graph 508, a third uptime graph 510, and a fourth uptime graph 512.

In one embodiment, region selection 502 may be interacted with by a user to submit a selection of a geospatial region for which instrument data should be displayed. In an example embodiment, region selection 502 may include one or more of country, region, state, district, city, zip code, warranty status, instrument type, or other criteria that may be applied to a search to filter results to a desired set of instruments. In one embodiment, export button 504 may be used to export displayed data in various formats. In one embodiment, first uptime graph 506 may describe uptime of the selected instruments during a 24 hour period. In one embodiment, second uptime graph 508 may describe uptime of the selected instruments during a 10 day period. In one embodiment, third uptime graph 510 may describe uptime of the selected instruments during a 30 day period. In one embodiment, fourth uptime graph 512 may describe uptime of the selected instruments during a 90 day period. In an example embodiment, only a single uptime graph is shown at a time based on a user selection for a time period. In an example embodiment, each uptime graph may be shown with one or more of a comparison graph line showing uptime for a high uptime comparison set of instruments, and a comparison graph line showing uptime for a low uptime comparison set of instruments. In an example embodiment, each uptime graph may include a graph line showing uptime of selected instruments, $90^{th}$ percentile instrument uptime, and $50^{th}$ percentile instrument uptime.

Figures 5B, 5C:
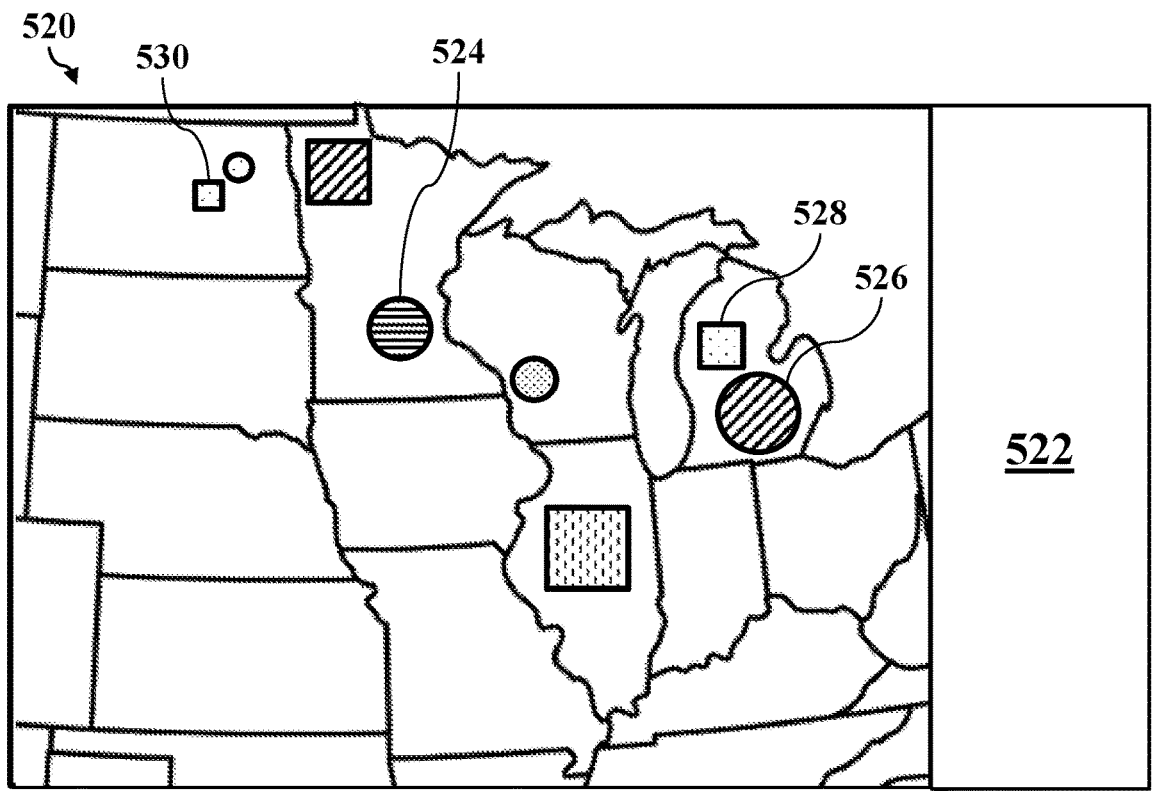
FIG. 5B is a diagram showing an exemplary maintenance map interface that may be provided as part of the geospatial maintenance interface of FIG. 4.
FIG. 5C is a diagram showing an exemplary detailed maintenance interface that may be provided as part of the geospatial maintenance interface of FIG. 4.

FIG. 5B is a diagram showing an exemplary maintenance map interface 520 that may be provided as part of the geospatial maintenance interface of FIG. 4. The maintenance map interface 520 includes a set of map information 522, a first maintenance indicator 524, a second maintenance indicator 526, a third maintenance indicator 528, and a fourth maintenance indicator 530.

In one embodiment, map information 522 may include information describing the displayed map or region, and describing symbols shown on the map. In one embodiment, map indicators may indicate one or more of a maintenance type, maintenance location, maintenance volume, and maintenance immediacy. In an example embodiment, first maintenance indicator 524 may be of a shape indicating the type of maintenance need. In one example embodiment, a circular shape may indicate an actual maintenance need identified in FIG. 3A. In an example embodiment, first maintenance indicator 524 may include a visual element indicating an immediacy of a maintenance need. In an example embodiment, first maintenance indicator 524 may have one or more of a color, pattern, texture, or animation indicating a critical maintenance need. In an example embodiment, a critical maintenance need may be an overdue maintenance need. In an example embodiment, first maintenance indicator 524 may have a size corresponding to a number of instruments having maintenance needs at the location at which the indicator is shown.

In an example embodiment, second maintenance indicator 526 may have a different size, shape, color, or animation than first maintenance indicator 524. In an example embodiment, second maintenance indicator 526 may be larger indicating more instruments having maintenance needs, and may have a different visual design indicating a less immediate maintenance need.

In an example embodiment, third maintenance indicator 538 may be square, which may indicate a potential maintenance need. In an example embodiment, third maintenance indicator 528 may be a small square indicating a lower quantity of instruments having a maintenance need, or may have a visual design indicating a low immediacy of maintenance need, or both. In an example embodiment, fourth maintenance indicator 530 may be relatively smaller than third maintenance indicator 528 indicating an even smaller number of instruments having a maintenance need. In an example embodiment, maintenance indicator symbols and designs may have other sizes, shapes, colors, and visual characteristics as will be apparent to one of ordinary skill in the art in light of this disclosure. In one embodiment, hovering over or clicking on a maintenance indicator may provide more information relating to the symbol. In an example embodiment, such information may be displayed in set of map information 522. In an example embodiment, information may be displayed as a pop up window. In an example embodiment, displayed information may include one or more of number of instruments, number of maintenance needs, deadline ranges of maintenance needs, locations of instruments, and other information.

FIG. 5C is a diagram showing an exemplary detailed maintenance interface 540 that may be provided as part of the geospatial maintenance interface of FIG. 4. The detailed maintenance interface 540 includes a task description column 542, a device column 544, a maintenance status 546, a first maintenance indicator 548, a second maintenance indicator 550, a third maintenance indicator 552, a fourth maintenance indicator 554, an immediacy pointer 556, and a device browser 558. In one embodiment, task description column 542 may describe a maintenance need shared by a number of instruments. In one embodiment, task description column 542 may categorize maintenance needs by actual maintenance needs ("AMT") and potential maintenance needs ("PMT").

In one embodiment, device column 544 may show for an instrument whether a maintenance need exists for each shared type of maintenance need. In one embodiment, a device column 544 may be displayed or may be displayable for each instrument matching a search criteria. In one embodiment, device browser 558 may be used to navigate through or browse each viewable device column 544. In one embodiment, each device column may include a maintenance status 546. In an example embodiment, maintenance status 546 may be displayed as a bar graph with each section of the bar graph indicating a different immediacy of the maintenance need. In an example embodiment, each device column 544 may have a number of maintenance status 546 corresponding to the number of shared maintenance needs in task description column 542.

In an example embodiment, first maintenance indicator 548 may indicate a most immediate need, second maintenance indicator 550 may indicate a next most immediate need, third maintenance indicator 552 may indicate a next most immediate need, and fourth maintenance indicator 554 may indicate a least immediate need. In one embodiment, immediacy pointer 556 may be positioned appropriately on each maintenance status 546 to indicate a deadline associated with the particular maintenance need for that instrument. In an example embodiment, first indicator 548 may correspond to an overdue maintenance need, second indicator 550 may correspond to a maintenance need due within 7 days, third indicator 552 may correspond to a maintenance need due within 8 to 21 days, and fourth indicator 554 may correspond to a maintenance need not due until at least 21 days.

In an example embodiment, device column 544 for "Device 1" may include a maintenance status for an actual maintenance need "Ultrasonic Tips" having an immediacy pointer indicating a maintenance deadline within 5 days, a need for "Aspirate Tubing" maintenance within 15 days, and a need for "Vacuum Pumps" due immediately. In an example embodiment, an immediate need for "Vacuum Pumps" may indicate that, based upon a number of testing cycles performed with "Device 1" since a preceding pump maintenance, the Vacuum Pump has an immediate need for interval based maintenance. In an example embodiment, a Vacuum Pump maintenance may include replacing a seal or hose, cleaning an inlet or outlet portion, or oiling a moving portion.

In an example embodiment, device column 544 for "Device 1" may include a maintenance need for "Vacuum Pump 1" within 30 days, a need for "Vacuum Pump 2" within 15 days, and a need for "Compressor Pump" within 5 days. In an example embodiment, a need for "Compressor Pump" maintenance within 5 days may indicate that a comparison of that pumps current performance in flow rate or power consumption to a historic performance value shows a significant change in performance suggesting that a failure of the "Compressor Pump" or a related component may occur within a certain time frame. In an example embodiment, "Compressor Pump" maintenance may include inspecting and cleaning the compressor pump and related components to determine if corrective maintenance of those components may return the "Compressor Pump" to previous performance levels or prevent further degradation of performance.

In an example embodiment, a maintenance technician performing maintenance on "Device 1," or a maintenance supervisor assigning technicians to "Device 1," may view device column 544 for "Device 1" and schedule all maintenance needs that will arise or may arise in the next 21 days to be performed on a single day, rather than returning multiple times as each becomes more immediately necessary. In an example embodiment, a maintenance technician performing interval based maintenance on "Device 1" for "Vacuum Pumps" may also perform interval based maintenance on "Ultrasonic Tips," and may also perform corrective maintenance for potential problems with "Compressor Pump." In an example embodiment, by addressing multiple immediate and upcoming maintenance needs in a single trip to "Device 1", a technician may be able to avoid one or more future trips thereby reducing travel time and increasing efficiency.

Figure 6:
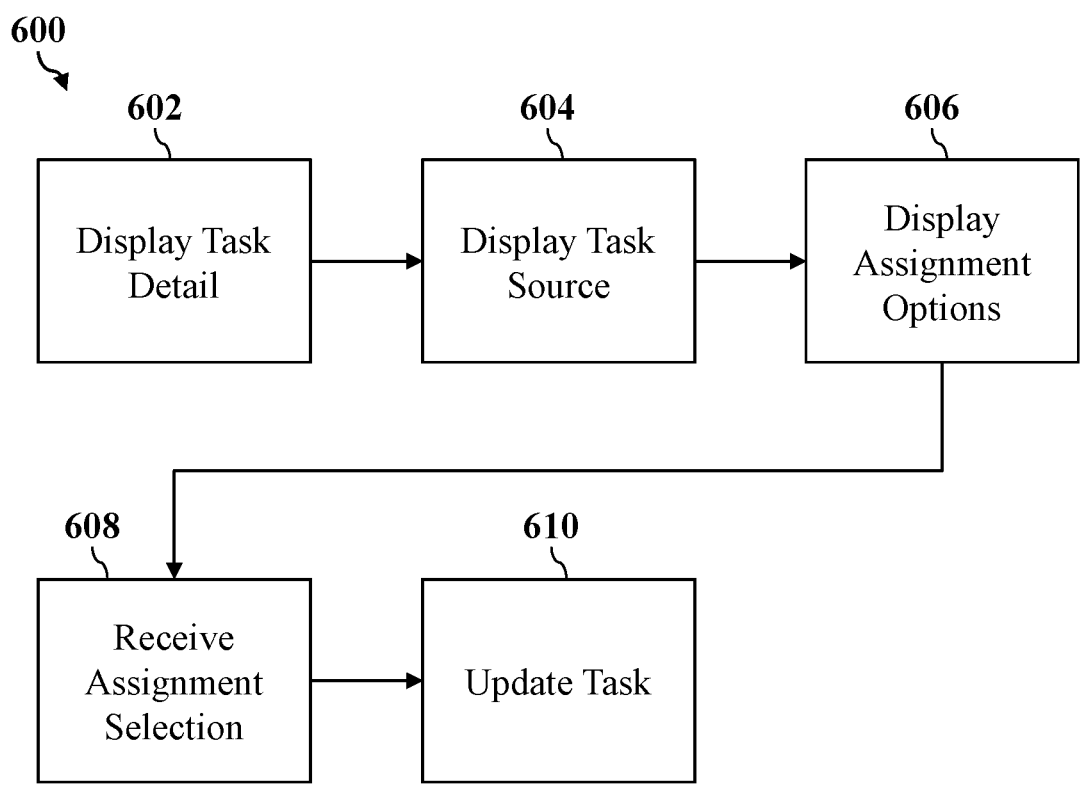
FIG. 6 is a flowchart showing an exemplary process which may be used in some embodiments to assign maintenance tasks to technicians.

FIG. 6 is a flowchart showing an exemplary process 600 which may be used in some embodiments to assign maintenance tasks to technicians. In an example embodiment, process 600 may be performed by or with maintenance system 10. In a step 602, a set of task details are displayed. In a step 604, a task source is displayed. In a step 606, a set of assignment options is determined and displayed. In a step 608, an assignment selection is received. In a step 610, an associated task is updated.

In one embodiment, displaying task detail at step 602 may include, when a user interacts with a portion of geospatial interface 102 that describes a maintenance need or task, displaying additional information relating to that maintenance need. In an example embodiment, when a user interacts with device 544 information may be displayed describing the particular maintenance need, a time associated with addressing the maintenance need, and the date of the maintenance deadline. In one embodiment, displaying a task source at step 604 may include, when task details are displayed, indicating whether the task is an actual maintenance need or a potential maintenance need.

In one embodiment, displaying assignment options at step 606 may include displaying one or more options for addressing a maintenance need. In an example embodiment, options may include providing an option to select one or more technicians from a list of technicians to assign to the maintenance need. In an example embodiment, a list of maintenance technicians may be determined and presented based upon one or more of a location of the affected instrument, current location of the technician, other tasks already assigned to the technician, and other maintenance needs within a configured distance of the selected maintenance need. In an example embodiment, the list of maintenance technicians may only include those that are within a configured distance of the instrument, and that have the availability of time to address each upcoming maintenance task associated with that instrument, or each upcoming maintenance task associated with any instrument at the location of that instrument. In an example embodiment, a technician's current location may be determined based upon data received from technician device 106. In an example embodiment, the list of maintenance technicians may be sorted in order of efficiency and minimization of travel time. In an example embodiment, maintenance server 100 may automatically assign the most efficient and available technician to maintenance tasks as they are added to the system.

In one embodiment, when an assignment selection is received at step 608, an associated maintenance need or task may be updated such as at step 610 to reflect that a resource has been assigned to address that task. In one embodiment, assignment selections may be received automatically based upon a selection by the maintenance server 100 of an efficient technician for a task, or semi-automatically based upon lists of technicians presented to users for selection. In one embodiment, updating 610 a task to reflect assignment may include changing one or more records on maintenance server 100, or providing notifications. In an example embodiment, this may include updating records of a ticketing software of maintenance server 100. In an example embodiment, this may include providing a notification to technician device 106 of such a change.

Explicit Definitions

When appearing in the claims, a statement that something is "based on" something else should be understood to mean that something is determined at least in part by the thing that it is indicated as being "based on." When something is required to be completely determined by a thing, it will be described as being "based exclusively on" the thing.

When used in the claims, "determining" should be understood to refer generating, selecting, defining, calculating or otherwise specifying something. For example, to obtain an output as the result of analysis would be an example of "determining" that output. As a second example, to choose a response from a list of possible responses would be a method of "determining" a response. As a third example, to identify data received from an external source (e.g., a microphone) as being a thing would be an example of "determining" the thing.

When used in the claims, a "diagnostic instrument", "lab instrument", or "instrument" should be understood to refer to any tool, machine, equipment, device, or combination of one or more thereof, whether fully or partially located within a laboratory (e.g., one portion of the lab instrument may be within a laboratory while another portion may be hosted in the cloud), or fully or partially located elsewhere, that may be used or may be configured to be used as recited in the claims.

When used in the claims a "a means for providing a geospatial interface that shows upcoming maintenance requirements of a plurality of instruments" should be understood as a means plus function limitation as provided for in 35 U.S.C. § 112(f), in which the function is "providing a geospatial interface that shows upcoming maintenance requirements of a plurality of instruments" and the corresponding structure is a server configured to perform processes as illustrated in FIGS. 2-4 and described in the corresponding text.

The invention claimed is:

1. A method comprising:
   a) receiving a set of instrument use data and a set of instrument performance data from a plurality of instruments located in a specific region or multiple regions;
   b) determining, for each of the plurality of instruments, whether there are any upcoming maintenance requirements based on the set of instrument use data and the set of instrument performance data; and
   c) based on the upcoming maintenance requirements, providing to a user an interface of the plurality of instruments and a mapping of the upcoming maintenance requirements in the specific region or multiple regions for maintenance to be performed on the plurality of instruments wherein the interface comprises:
      i) a task description column, the task description column comprising both actual maintenance needs and potential maintenance needs of a set of devices from the plurality of devices in the specific region or multiple regions;
      ii) a set of device columns, wherein, for each device columns from the set of device columns:
         A) that device column corresponds to a device from the set of devices;
         B) that device column comprises a set of rows, wherein each row from the set of rows corresponds to an actual maintenance need or a potential maintenance need from the task description column; and
      C) each row in that device column comprises:
         I) a set of maintenance indicators corresponding to time periods when the actual or potential maintenance need corresponding to that row is due for the device corresponding to that device column; and
         II) a pointer icon indicating a deadline for the actual or potential maintenance need corresponding to that row for the device corresponding to that device column.

2. The method of claim 1, wherein:
   a) the set of instrument use data comprises, for each instrument of the plurality of instruments, a usage indicator describing a number of test cycles performed by that instrument during a period of time;
   b) the set of instrument performance data comprises, for each instrument of the plurality of instruments, a performance indicator that describes the operational performance of a component of that instrument; and
   c) the performance indicator is selected from the group consisting of:
      i) flow rate of a pump,
      ii) temperature of an electrical component, and
      iii) power consumption of an electrical component.

3. The method of claim 1, further comprising:
   a) displaying a map of the specific region or multiple regions;
   b) displaying a first set of symbols on the map, wherein each symbol of the first set of symbols indicates a location and a number of actual maintenance requirements, and wherein the actual maintenance requirements are selected from the upcoming maintenance requirements; and
   c) displaying a second set of symbols on the map, wherein each symbol of the second set of symbols indicates a location and a number of potential maintenance requirements, wherein the potential maintenance requirements are selected from the upcoming maintenance needs;
   wherein each symbol of the first set of symbols comprises a size that is determined based upon the number of actual maintenance requirements at the location.

4. The method of claim 1, further comprising:
   a) displaying a first graph line showing an uptime for the plurality of instruments over a period of time;
   b) displaying a second graph line showing, over the period of time, an uptime for a set of high uptime instruments; and
   c) displaying a third graph line showing, over the period of time, an uptime for a set of low uptime instruments.

5. The method of claim 1, further comprising:
   a) displaying a device maintenance view for each instrument of the plurality of instruments;
   b) displaying a set of maintenance requirements and displaying a set of maintenance statuses for each instrument of the plurality of instruments, wherein:
      i) each of the set of maintenance statuses is associated with a maintenance requirement of the set of maintenance requirements; and
      ii) each of the set of maintenance statuses comprises an indicator positioned on that maintenance status that indicates an immediacy of that maintenance requirement.

6. The method of claim 1, wherein the upcoming maintenance requirements comprise a set of actual maintenance requirements and a set of potential maintenance requirements, further comprising:
 a) identifying the set of actual maintenance requirements based on the set of instrument use data; and
 b) identifying the set of potential maintenance requirements based on the set of instrument performance data.

7. The method of claim 1, wherein the upcoming maintenance requirements comprise a set of potential maintenance requirements, further comprising:
 a) maintaining a set of historical performance data for each instrument of the plurality of instruments;
 b) after new performance data is received for an instrument of the plurality of instruments, comparing the new performance data to the set of historical performance data for that instrument to determine a performance change; and
 c) where the performance change indicates a significant change, adding a potential maintenance requirement to the set of potential maintenance requirements, wherein the potential maintenance requirement is associated with that instrument and describes a component of that instrument associated with the performance change.

8. The method of claim 7, further comprising:
 a) determining a first standard deviation of the set of historical performance data for that instrument over a first period of time;
 b) determining a second standard deviation of the new performance data for that instrument over a second period of time; and
 c) determining that the performance change indicates a significant change when the difference between the first standard deviation and the second standard deviation exceeds a configured threshold.

9. The method of claim 7, wherein the set of historical performance data comprises performance data associated with one or more components of that instrument, further comprising:
 a) determining the performance change for each component of the one or more components; and
 b) when adding the potential maintenance requirement for the component, determining a priority for the potential maintenance requirement based on the magnitude of the performance change and a type of the component.

10. A non-transitory computer readable medium storing instructions operable to, when executed, cause a processor to perform a method comprising:
 a) receiving a set of instrument use data and a set of instrument performance data from a plurality of instruments located in a specific region or multiple regions;
 b) determining, for each of the plurality of instruments, whether there are any upcoming maintenance requirements based on the set of instrument use data and the set of instrument performance data; and
 c) based on the upcoming maintenance requirements, providing to a user an interface of the plurality of instruments and a mapping of the upcoming maintenance requirements in the specific region or multiple regions for maintenance to be performed on the plurality of instruments wherein the interface comprises:
   i) a task description column, the task description column comprising both actual maintenance needs and potential maintenance needs of a set of devices from the plurality of devices in the specific region or multiple regions; and
   ii) a set of device columns, wherein, for each device columns from the set of device columns:
     A) that device column corresponds to a device from the set of devices;
     B) that device column comprises a set of rows, wherein each row from the set of rows corresponds to an actual maintenance need or a potential maintenance need from the task description column; and
     C) each row in that device column comprises:
       I) a set of maintenance indicators corresponding to time periods when the actual or potential maintenance need corresponding to that row is due for the device corresponding to that device column; and
       II) a pointer icon indicating a deadline for the actual or potential maintenance need corresponding to that row for the device corresponding to that device column.

11. The medium of claim 10, wherein:
 a) the set of instrument use data comprises, for each instrument of the plurality of instruments, a usage indicator describing a number of test cycles performed by that instrument during a period of time;
 b) the set of instrument performance data comprises, for each instrument of the plurality of instruments, a performance indicator that describes the operational performance of a component of that instrument; and
 c) the performance indicator is selected from the group consisting of:
   i) flow rate of a pump,
   ii) temperature of an electrical component, and
   iii) power consumption of an electrical component.

12. The medium of claim 10, wherein the method further comprises:
 a) displaying a map of the specific region or multiple regions;
 b) displaying a first set of symbols on the map, wherein each symbol of the first set of symbols indicates a location and a number of actual maintenance requirements, and wherein the actual maintenance requirements are selected from the upcoming maintenance requirements; and
 c) displaying a second set of symbols on the map, wherein each symbol of the second set of symbols indicates a location and a number of potential maintenance requirements, wherein the potential maintenance requirements are selected from the upcoming maintenance needs;
 wherein each symbol of the first set of symbols comprises a size that is determined based upon the number of actual maintenance requirements at the location.

13. The medium of claim 10, wherein the method further comprises:
 a) displaying a first graph line showing an uptime for the plurality of instruments over a period of time;
 b) displaying a second graph line showing, over the period of time, an uptime for a set of high uptime instruments; and
 c) displaying a third graph line showing, over the period of time, an uptime for a set of low uptime instruments.

14. The medium of claim 10, wherein the method further comprises:
 a) displaying a device maintenance view for each instrument of the plurality of instruments;

b) displaying a set of maintenance requirements and displaying a set of maintenance statuses for each instrument of the plurality of instruments, wherein:
  i) each of the set of maintenance statuses is associated with a maintenance requirement of the set of maintenance requirements; and
  ii) each of the set of maintenance statuses comprises an indicator positioned on that maintenance status that indicates an immediacy of that maintenance requirement.

15. The medium of claim 10, wherein the upcoming maintenance requirements comprise a set of actual maintenance requirements and a set of potential maintenance requirements, and wherein the method further comprises:
  a) identifying the set of actual maintenance requirements based on the set of instrument use data; and
  b) identifying the set of potential maintenance requirements based on the set of instrument performance data.

16. The medium of claim 10, wherein the upcoming maintenance requirements comprise a set of potential maintenance requirements, and wherein the method further comprises:
  a) maintaining a set of historical performance data for each instrument of the plurality of instruments;
  b) after new performance data is received for an instrument of the plurality of instruments, comparing the new performance data to the set of historical performance data for that instrument to determine a performance change; and
  c) where the performance change indicates a significant change, adding a potential maintenance requirement to the set of potential maintenance requirements, wherein the potential maintenance requirement is associated with that instrument and describes a component of that instrument associated with the performance change.

17. The medium of claim 16, wherein the method further comprises:
  a) determining a first standard deviation of the set of historical performance data for that instrument over a first period of time;
  b) determining a second standard deviation of the new performance data for that instrument over a second period of time; and
  c) determining that the performance change indicates a significant change when the difference between the first standard deviation and the second standard deviation exceeds a configured threshold.

18. The medium of claim 16, wherein the set of historical performance data comprises performance data associated with one or more components of that instrument, and wherein the method further comprises:
  a) determining the performance change for each component of the one or more components; and
  b) when adding the potential maintenance requirement for the component, determining a priority for the potential maintenance requirement based on the magnitude of the performance change and a type of the component.

* * * * *